(12) United States Patent
Murayama et al.

(10) Patent No.: US 7,575,559 B2
(45) Date of Patent: Aug. 18, 2009

(54) GUIDE WIRE

(75) Inventors: Hiraku Murayama, Fujinomiya (JP); Katsuro Mishima, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 54 days.

(21) Appl. No.: 10/809,901

(22) Filed: Mar. 26, 2004

(65) Prior Publication Data

US 2005/0027214 A1 Feb. 3, 2005

(30) Foreign Application Priority Data

Mar. 27, 2003 (JP) .............................. 2003-087977

(51) Int. Cl.
*A61M 25/00* (2006.01)
(52) U.S. Cl. ..................................................... 600/585
(58) Field of Classification Search ................. 600/585
See application file for complete search history.

(56) References Cited

U.S. PATENT DOCUMENTS

| 5,171,383 | A |   | 12/1992 | Sagae et al. |         |
|-----------|---|---|---------|--------------|---------|
| 5,213,111 | A | * | 5/1993  | Cook et al.  | 600/585 |
| 6,001,068 | A |   | 12/1999 | Uchino et al.|         |
| 6,093,157 | A | * | 7/2000  | Chandrasekaran | 600/585 |
| 6,482,166 | B1| * | 11/2002 | Fariabi      | 600/585 |
| 6,488,637 | B1| * | 12/2002 | Eder et al.  | 600/585 |

FOREIGN PATENT DOCUMENTS

| JP | 3-115653    | 11/1991 |
| JP | 04-183845   | 6/1992  |
| JP | 5-63554     | 8/1993  |
| JP | 11-061372   | 3/1999  |
| JP | 2001-314513 | 11/2001 |

\* cited by examiner

*Primary Examiner*—Max Hindenburg
*Assistant Examiner*—Jeffrey G Hoekstra
(74) *Attorney, Agent, or Firm*—Buchanan Ingersoll & Rooney PC

(57) ABSTRACT

A guide wire includes a distal end portion and a main body portion, wherein the main body portion includes a center layer formed of a first material, a surface layer formed of a second material, and an intermediate layer formed of a mixture of the first material and the second material.

11 Claims, 7 Drawing Sheets

GUIDE WIRE

BACKGROUND OF THE INVENTION

The present invention relates to a guide wire, particularly to a guide wire for use in introducing a catheter into a body lumen such as a blood vessel.

Guide wires are used to guide a catheter in treatment of cites at which open surgeries are difficult or which require low invasiveness to the body, for example, PTCA (Percutaneous Transluminal Coronary Angioplasty), or in diagnosis such as cardioangiography, and for the like purposes.

A guide wire used in the PTCA procedure is inserted, with its distal end projecting from the distal end of a balloon catheter, into the vicinity of a target angiostenosis portion together with the balloon catheter, and is thus used to guide the distal end portion of the balloon catheter to the vicinity of the target angiostenosis portion.

Particularly, a guide wire used to insert a balloon catheter into a blood vessel is required to go forward in a complicatedly meandering blood vessel, and is therefore required to have sufficient flexibility and restoring performance against bending, pushability and torque transmission performance (these are altogether called operationality) for securely transmitting an operational force from the proximal end portion to the distal end side, kink resistance, and the like.

In the conventional guide wires, the core member is substantially made of a single material. Therefore, the flexibility of the distal end portion of the guide wire is lost where a material having a comparatively high elastic modulus is used for forming the core member in order to enhance the operationality of the guide wire. On the other hand, if a material having a comparatively low elastic modulus is used for the core member in order to obtain flexibility at the distal end portion of the guide wire, the operationality on the proximal end side of the guide wire is lost. Thus, it has been regarded as difficult to satisfy both the requirements of flexibility and operationality by using a core member made of a single material.

U.S. Pat. No. 5,171,383 proposes a guide wire in which an Ni-Ti alloy wire is used as a core member, and the distal end side and the proximal end side of the alloy wire are heat-treated under different conditions in order to enhance flexibility of a distal end portion of the guide wire and to enhance rigidity on the proximal end side of the guide wire.

In addition, U.S. Pat. No. 6,001,068 proposes a guide wire which is comprised of a flexible wire disposed on the distal end side, a high rigidity wire disposed on the proximal end side, and a tubular joint member having a groove and a slit for connection between the first wire and the second wire, wherein the joint member is gradually raised in rigidity from the distal end side toward the proximal end side thereof.

SUMMARY OF THE INVENTION

This invention provides a guide wire that comprises a distal end portion and a main body portion, wherein said main body portion comprises a center layer formed of a first material, a surface layer formed of a second material, and an intermediate layer formed of a mixture of said first material and said second material.

This invention provides a guide wire that comprises a distal end portion, a main body portion, and an intermediate portion located between said distal end portion and said main body portion, said intermediate portion comprises a center layer formed of a first material, and a surface layer formed of a mixture of said first material and a second material.

This invention provides a guide wire that comprises a distal end portion and a main body portion, wherein said main body portion comprises a center layer formed of a first material, a surface layer formed of a second material, and an intermediate layer formed of a mixture of said first material and said second material, said intermediate layer is increased in the content of said first material toward said center layer, wherein said first material is a first metallic material, and said second material is a second metallic material higher in rigidity than said first metallic material.

DETAILED DESCRIPTION OF THE PREFERRED EMBODIMENTS

Figure 1:
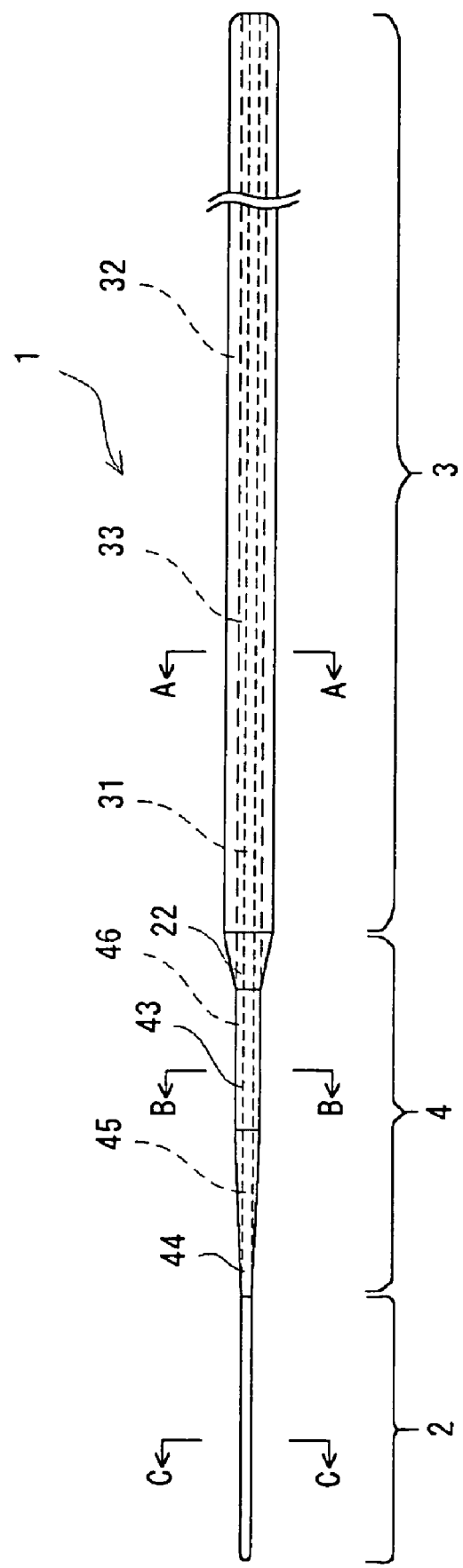
FIG. 1 is a front view of a guide wire according to one embodiment of the present invention.

A guide wire according to an embodiment of the present invention will be described referring to the accompanying drawings.

The guide wire 1 according to the present invention is a guide wire including a distal end portion 2 and a main body portion 3. The main body portion 3 includes a center layer 31 formed of a first material, a surface layer 32 formed of a second material, and an intermediate layer 33 formed of a mixture of the first material and the second material.

Therefore, the guide wire has combined properties of the first material and the second material. Accordingly, the guide wire has intermediate physical properties, as compared with guide wires formed only of the first material or formed only of the second material, and shows high operationality.

As shown in FIG. 1, the guide wire, like the guide wire 1 in this embodiment shown in the figure, preferably includes the distal end portion 2, the main body portion 3, and an intermediate portion 4 disposed between the portions 2 and 3. Furthermore, the distal end portion 2 is formed of the first material, and is continuous with a central portion of the main body portion 3. The intermediate portion 4 preferably includes a center layer 45 formed of the first material, and a surface layer 46 formed of a mixture of the first material and the second material.

In addition, the intermediate layer 33 formed of the mixture of the first material and the second material of the main body portion 3 is preferably decreased in the content of the first material toward the surface layer 32 and increased in the content of the second material toward the surface layer 32 is approached. As in this embodiment, the guide wire is preferably an integral body which does not have any joint portion.

The guide wire 1 is a medical guide wire to be used in the state of being inserted in a catheter (not shown). As shown in FIG. 1, the guide wire 1 includes the distal end portion 2, the main body portion 3, and the intermediate portion 4 disposed between the distal end portion 2 and the main body portion 3. The overall length of the guide wire 1 is not particularly limited, it being preferably about 200 to 5000 mm.

Figure 4:
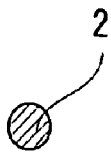
FIG. 4 is a sectional view taken along line C-C of FIG. 1.

The distal end portion 2, in the guide wire 1 in this embodiment, is a small-diameter portion for forming the distal end of the guide wire, a shown in FIG. 1. The length of the distal end portion 2 is preferably about 20 to 100 mm, particularly about 5 to 30 mm. The diameter of the distal end portion 2 is preferably about 0.04 to 0.2 mm. Incidentally, the distal end portion 2 may have a substantially constant diameter over the whole length thereof, or the distal end portion 2 as a whole is reduced in diameter in a tapered form toward the distal end side. In this guide wire 1, the distal end portion 2 is formed only of the first material, as shown in FIG. 4. The distal end portion 2 may includes a thin surface coating layer formed of the second material (described later) at the surface thereof.

As the first material, a metal is preferably used. As the metal, preferred is an Ni—Ti based alloy or a contrast metal. Examples of the contrast metal include noble metals such as gold, platinum, and tungsten, and alloys containing these noble metals. With a high-contrast metal thus used as the first material, it is possible to insert the guide wire into a living body while confirming the position of the distal end portion by radiography, echography or the like.

In addition, it is preferable to use an Ni—Ti based alloy capable of showing pseudo-elasticity, as the first metallic material. With the first material constituted of such an alloy, the distal end portion becomes a flexible portion. When a metallic material capable of showing pseudo-elasticity (also called pseudo-elastic alloy) is used as the first metallic material, a high compliance performance in relation to a complicatedly curved blood vessel and high operationality can be obtained because the material has sufficient flexibility and restoring performance. Besides, the high restoring performance of the pseudo-elastic alloy ensures that the distal end portion 2 will not acquire a nearly permanent bend even when subjected to repeated curving or bending, so that the operationality of the guide wire 1 can be prevented from being lowered due to a nearly permanent bend.

The pseudo-elastic alloys include those showing any tensile stress-strain curves, and include not only those whose transformation points such as As, Af, Ms, and Mf can be measured conspicuously but also those whose transformation points cannot be measured conspicuously. Thus, the pseudo-elastic alloys include all of those which are largely deformed (strained) under a stress and which substantially restore the original shape thereof upon removal of the stress.

Examples of the metallic material capable of showing pseudo-elasticity include Ni—Ti based alloys, Cu—Zn alloys, Cu—Zn—X alloys (where X is at least one of Be, Si, Sn, Al, and Ga), and Ni-Al alloys. Specifically, preferable examples include Ni—Ti based alloys such as Ni—Ti alloys containing 49 to 52 at % of Ni, Cu—Zn alloys containing 38.5 to 41.5 wt % of Zn, Cu—Zn—X alloys (where X is at least one of Be, Si, Sn, Al, and Ga) containing 1 to 10 wt % of X, and Ni—Al alloys containing 36 to 38 at % of Al. As the first metallic material, particularly preferred are the Ni—Ti based alloys.

In the guide wire 1 in this embodiment, as shown in FIG. 1, the intermediate portion 4 includes a cylindrical portion 43 continuous with the distal end of the main body portion 3, and a second tapered portion 44 formed on the distal side of the cylindrical portion 43 and gradually reduced in diameter toward the distal end thereof.

With this configuration, since the rigidity of the intermediate portion 4 is gradually lowered toward the distal end, the compliance of the guide wire 1 in relation to a blood vessel and safety are enhanced, and the guide wire 1 is less susceptible to kinking or the like. Incidentally, while one tapered portion reduced in diameter toward the distal end is provided in this embodiment of the present invention, two or more tapered portions may be provided. Besides, the intermediate portion 4 as a whole may be a tapered portion gradually reduced in diameter toward the distal end portion 2.

Figure 3:
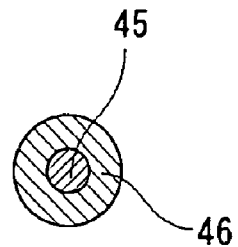
FIG. 3 is a sectional view taken along line B-B of FIG. 1.

As shown in FIGS. 1 and 3, the intermediate portion 4 preferably includes a center layer 45 and a surface layer 46. Particularly, it is preferable that the center layer 45 is formed of the above-mentioned first material and is continuous with the distal end portion 2. The surface layer 46 is preferably formed of a mixture of the above-mentioned first material and the second material which will be described later. In this embodiment, the diameter of the center layer 45 is nearly equal to the diameter of the distal end portion 2. The length of the intermediate portion 4 is preferably about 10 to 200 mm, particularly about 30 to 100 mm.

The second material is preferably a material higher in rigidity than the first material forming the distal end portion. Specifically, the second material is preferably higher in elastic modulus (Young's modulus (modulus of longitudinal elasticity), shear modulus (modulus of transverse elasticity), bulk modulus) than the first material. As the second material, various metallic materials such as stainless steels (for example, SUS304, SUS303, SUS316, SUS316L, SUS316 J1, SUS316J1L, SUS405, SUS430, SUS434, SUS444, SUS429, SUS430F, SUS302, etc.), high-carbon steels, and cobalt-based alloys can be used. Among these, particularly preferred are stainless steels and cobalt-based alloys. As a combination of the first material and the second material, preferred are combinations in which any of the above-mentioned Ni—Ti based alloys is used as the first material and any of the above-mentioned stainless steels is used as the second material.

The surface layer 46 of the intermediate potion 4 is formed of a mixture of a first material and a second material. The first material and the second material are as described above. The weight ratio of the first material to the second material in the material for forming the surface layer 46, which depends on the materials used, is preferably in the range of from 1:9 to 9:1, more preferably from 3:7 to 7:3.

Furthermore, the surface layer 46 is preferably decreased in the content of the first material toward the surface and increased in the content of the second material toward the surface. With this configuration, the guide wire 1 has gradient physical properties in the radial direction. The content of the second metallic material in the surface layer 46 may be increased stepwise or increased gradually toward the surface; further, the rate of increase in the content of the second metallic material may be increased or decreased toward the surface. In the guide wire 1 in this embodiment, the above-mentioned structure of the intermediate portion 4 extends to reach the main body portion 3 of the guide wire 1. Namely, the intermediate portion 4 of the guide wire 1 has at least the above-mentioned two-layer structure of the center layer 45 and the surface layer 46 over the whole length thereof.

The main body portion 3 includes the center layer 31 formed of the first material, the surface layer 32 formed of the second material, and the intermediate layer 33 formed of a mixture of the first material and the second material. The main body portion 3 includes a tapered portion 30 provided at a distal end portion thereof, and a main portion formed to have a substantially constant diameter. The length of the main body portion 3 is preferably about 300 to 5000 mm, particularly about 500 to 1000 mm. The diameter of the main body portion 3 is preferably about 0.2 to 1.2 mm.

Figure 2:
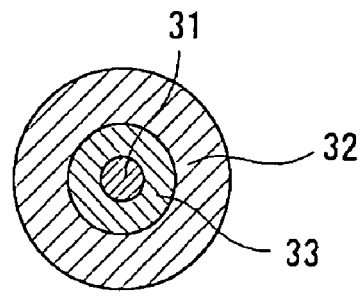
FIG. 2 is a sectional view taken along line A-A of FIG. 1.

As shown in FIG. 2, the main body portion 3 has a structure in which the center layer 31, the intermediate layer 33, and the surface layer 32 are provided in this order from the center side toward the outside. The center layer 31 is continuous with the above-described center layer 45 of the intermediate portion 4, and is formed of the above-described first material. In this guide wire 1, therefore, the center layer formed of the first material extends through the main body 3 and the intermediate layer 4, and forms the distal end portion 2. The first material is as described above.

The surface layer 32 forms an outer layer of the main body portion 3, and is formed of the second material which is different from the first material. As the second material, a metallic material is preferably used. Particularly, it is preferable that both the first material and the second material are metallic materials and that the second material is higher in rigidity than the first material.

The surface layer 32 of the main body portion 3 is preferably produced by use of the second metallic material higher in rigidity than the first metallic material which forms the distal end portion. Specifically, the second material is preferably higher in elastic modulus (Young's modulus (modulus of longitudinal elasticity), shear modulus (modulus of transverse elasticity), bulk modulus) than the first material. With the surface layer 32 of the main body portion 3 formed by use of the second metallic material having a high elastic modulus, the guide wire 1 becomes excellent in operationality (pushability and torque transmission performance).

As the second material, a variety of metallic materials such as stainless steels (for example, SUS304, SUS303, SUS316, SUS316L, SUS316J1, SUS316J1L, SUS405, SUS430, SUS434, SUS444, SUS429, SUS430F, SUS302, etc.), high-carbon steels, and cobalt-based alloys can be used. Particularly preferred are stainless steels and cobalt-based alloys. As a combination of the first material and the second material, preferred are combinations in which any of the above-mentioned Ni—Ti based alloys is used as the first material and any of the above-mentioned stainless steels is used as the second material.

The intermediate layer 33 of the main body portion 3 is formed of a mixture of the first material and the second material. The first material and the second material are as described above. The weight ratio of the first material to the second material in the material for forming the intermediate layer 33 depends on the materials used, and is preferably in the range of from 1:9 to 9:1, more preferably from 3:7 to 7:3.

Furthermore, the intermediate layer 33 is preferably decreased in the content of the first material toward the surface layer 32 and increased in the content of the second material toward the surface layer 32. As a result of this configuration, the guide wire has gradient physical properties in the radial direction. The content of the second metallic material in the intermediate layer 33 may be increased stepwise or increased gradually toward the surface layer 32; besides, the rate of increase in the content of the second metallic material may be increased or decreased toward the surface layer 32. In the guide wire 1 in this embodiment, the above-described structure extends to the proximal end of the guide wire 1. Namely, the main body portion 3 of the guide wire 1 as a whole has at least the above-mentioned three-layer structure of the center layer, the intermediate layer, and the surface layer.

Figure 5:
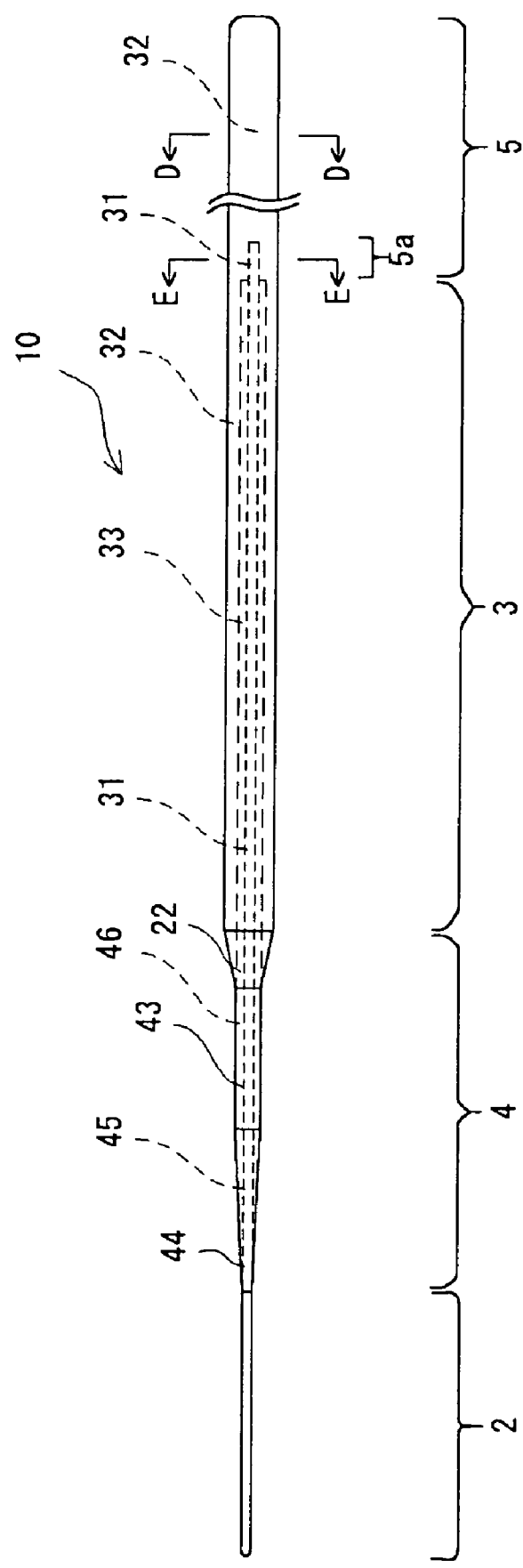
FIG. 5 is a front view of a guide wire according to another embodiment of the present invention.
Figure 6:
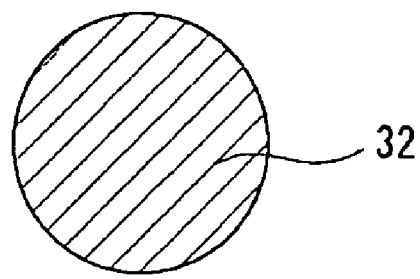
FIG. 6 is a sectional view taken along line D-D of FIG. 5.
Figure 7:
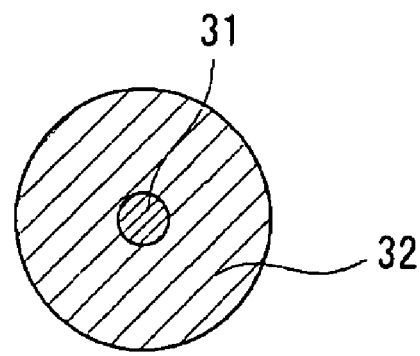
FIG. 7 is a sectional view taken along line E-E of FIG. 5.

This configuration, however, is not limitative, and, for example, a configuration as shown in FIGS. 5 to 7 may also be adopted.

FIG. 5 is a front view of a guide wire according to another embodiment of the present invention; FIG. 6 is a sectional view taken along line D-D of FIG. 5; and FIG. 7 is a sectional view taken along line E-E of FIG. 5.

The guide wire 10 according to this embodiment includes a proximal end portion 5 on the proximal end side of a main body portion 3.

As shown in FIG. 6, the proximal end portion 5 of the guide wire 10 is formed of the second material which forms a surface layer 32 of the main body portion 3. With the proximal end portion 5 of the guide wire 10 thus formed only of the second material, the operationality at the proximal end portion becomes good. In addition, it is preferable to provide a transition region 5a on the distal end side of the proximal end portion 5. As shown in FIG. 7, which is a sectional view taken along line E-E of FIG. 5, the transition region 5a is composed of a center layer 31 and a surface layer 32, and is free of any intermediate layer. Specifically, the center layer portion is the same as that in the main body portion 3, and the intermediate layer portion is formed of the second material, i.e., the same material as that which forms the surface layer 32. In other words, the transition region 5 has a structure in which the surface layer 32 is enlarged in thickness. Therefore, the transition region 5a is a portion which is slightly higher in rigidity than the three-layer structure portion (main body portion). With such a transition region provided, the operationality at the proximal end portion is enhanced.

The guide wire may have an outer surface coated with a resin. The resin is desirably a thermoplastic resin. Examples of the usable thermoplastic resin include olefin-based resins or polyolefin-based elastomers such as polyethylene, polypropylene, polybutene, ethylene-vinyl acetate copolymer, etc.; fluororesins or soft fluororesins; polyesters or polyester-based elastomers such as polyethylene terephthalate, polybutylene terephthalate, etc.; methacrylic resin; polyphenylene oxide; modified polyphenylene ether; polyurethane or polyurethane-based elastomers; polyamides or polyamide-based elastomers; polycarbonate; polyacetal; styrene-based resins or styrene-based elastomers such as polystyrene, stylene-butadiene copolymer, etc.; thermoplastic polyimides; and polyvinyl chloride. In addition, polymer alloys or polymer blends based on these resins may also be used. Furthermore, rubbers such as natural rubber, isoprene rubber, silicone rubbers, etc. may also be used. Among these materials, particularly preferred are the thermoplastic resins. Besides, the resin coating is preferably so flexible as not to hinder the curving of the guide wire, and the outer surface thereof is preferably a smooth surface free of ruggedness.

The outer surface of the resin coating may be coated with an anticoagulant such as heparin, urokinase, etc. or with an antithrombotiic material such as urethane-silicone block copolymer (registered trademark: Avcothane), hydroxyethyl methacrylate-styrene copolymer, etc.

A low friction material may be fixed to the surface of the resin coating. The fixation of the low friction material may be carried out only at a distal end portion or carried out at the portion exclusive of a proximal end portion. As the low friction material, there may be used hydrophobic materials having a low friction surface independently of wetting thereof, for example, fluororesins and silicone resins, and materials showing lubricity when wetted (lubricating materials). Specific examples of the latter include water-soluble polymeric materials and derivatives thereof. The lubricating material is fixed to the surface of the resin coating by covalent bond or ionic bond. The lubricating materials, on principle, are polymeric materials which are in a chain form free of cross-linkage and have a hydrophilic group such as —OH, —CONH$_2$, —COOH, —NH$_2$, —COO—, —SO$^3$—, etc. Furthermore, the lubricating materials are hydrated when wetted (for example, upon contact with blood), thereby developing lubricity.

Specifically, examples of natural water-soluble polymeric materials include starch-based ones such as carboxymethyl starch, dialdehyde starch, etc.; cellulose-based ones such as carboxymethyl cellulose, hydroxyethyl cellulose, etc.; tannin; lignin-based ones; alginic acid; gum arabic; polysaccharides such as heparin, chitin, chitosan, etc.; and proteins such as gelatin, casein, etc. Examples of synthetic water-soluble materials include polyvinyl alcohol; polyalkylene oxides such as polyethylene oxide; polyalkylene glycols such as polyethylene glycol; acrylic acid-based ones such as sodium polyacrylate; maleic anhydride-based ones such as methyl vinyl ether-maleic anhydride copolymer, sodium salt of methyl vinyl ether-maleic anhydride, ammonium salt of methyl vinyl ether-maleic anhydride, and ethyl ester maleate anhydride copolymer; phthalic acid-based ones such as polyhydroxyethyl phthalate; water-soluble polyesters such as polydimethylol propionate; acrylamide-based ones such as polyacrylamide hydrolyzate, quaternary product of polyacrylamide, etc.; polyvinyl pyrrolidone; polyethyleneimine; polyethylene sulfonate; and water-soluble nylon. Among these materials, preferred are the maleic anhydride-based ones, and particularly preferred is ethyl ester maleate anhydride copolymer.

Next, a guide wire according to a further embodiment of the present invention will be described referring to the accompanying drawings.

Figure 8:
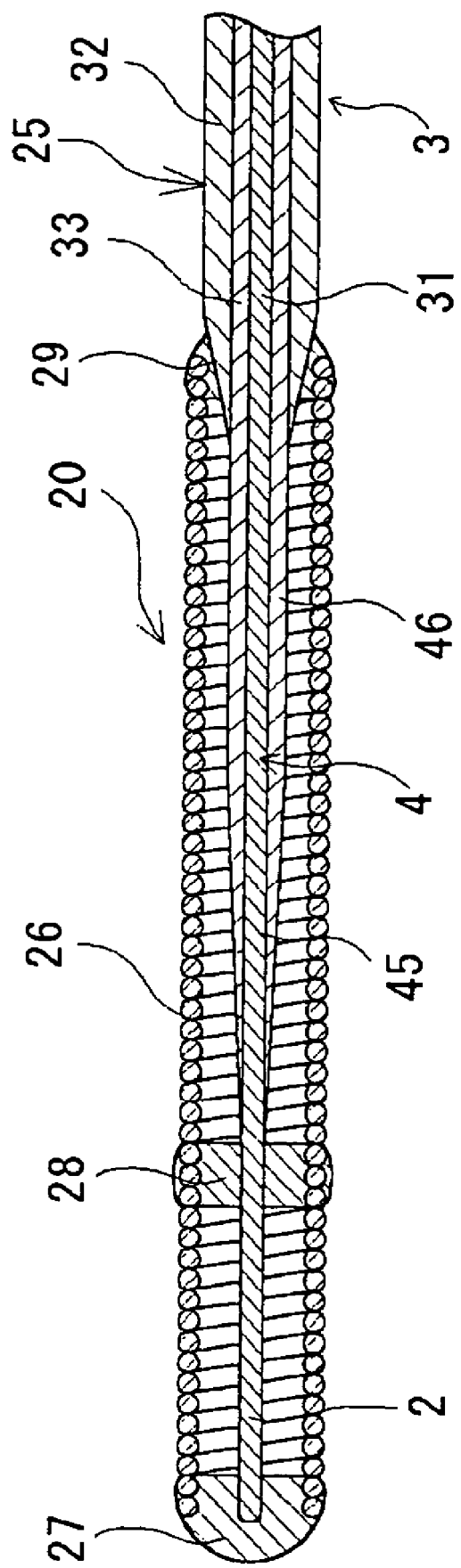
FIG. 8 is an enlarged sectional view of a distal end portion of a guide wire according to a further embodiment of the present invention.

FIG. 8 is an enlarged sectional view of a distal end portion of the guide wire according to the further embodiment of the present invention.

The guide wire 20 according to the present invention differs from the guide wire 1 only in that the guide wire 20 includes a coil portion 26 at a distal end portion thereof. The following description will be centered on the difference.

As shown in FIG. 8, the guide wire 20 is composed of a wire portion 25 and the coil portion 26. The wire portion 25 is the same as in the guide wire 1 described above, and description thereof is therefore omitted. In addition, the wire portion 25 according to the present invention may be replaced with the wire portion of the guide wire 10 described above.

As shown in FIG. 8, the guide wire 20 includes the coil portion 26 so provided as to cover a distal end portion of the guide wire 20.

The coil portion 26 is composed of a member obtained by spirally winding a filamentous material (thin wire), and is so disposed as to cover a small-diameter portion on the distal end side of a distal end portion 2. The coil portion 26 is preferably so disposed that a distal end portion of the distal end portion 2 does not make contact with the inside of the coil portion 26. In this embodiment, the small-diameter portion on the distal end side of the distal end portion 2 is inserted in a central portion of the coil portion 26, and does not make contact with the inside of the coil portion 26.

The coil portion 26 is preferably composed of a metallic material. Examples of the metallic material include stainless steels, superelastic alloys, cobalt-based alloys, noble metals such as gold, platinum, and tungsten, and alloys containing these metals. In addition, the coil portion is preferably made of a high contrast material. Preferred examples of the high contrast material include the above-mentioned noble metals such as gold, platinum, and tungsten. With the coil portion thus made of a high contrast material, it is possible to insert the guide wire into a living body while confirming the position of the distal end portion of the guide wire by radiography, echography or the like. In addition, the coil portion 26 may be formed by use of different materials on the distal end side and on the proximal end side. For example, the distal end side portion of the coil portion 26 may be made of a high contrast material while the proximal end side portion may be made of a material which is not highly radiopaque, such as stainless steel.

The coil portion 26 is fixed to the distal end portion 2 of the wire portion 25 at its distal end portion, and to a proximal end portion of the intermediate portion 4 at its proximal end portion. As shown in FIG. 8, the coil portion 26 is preferably fixed to the distal end portion 2 also at a position between the distal end portion and the proximal end portion thereof. The fixation is preferably carried out by soldering such as brazing, soldering, etc., welding, or adhesion by use of an adhesive. In this embodiment of the present invention, the coil portion 26 is fixed to the wire portion 25 respectively by fixing materials 27, 28, and 29 (solder, brazing filler metal). Besides, the distal end face of the fixing material 27 at the distal end portion is preferably formed in a rounded shape, in order to prevent it from damaging the inside wall of a blood vessel.

The overall length of the coil portion 26 is not particularly limited, it being preferably 5 to 500 mm, particularly 10 to 250 mm. The coil portion 26 preferably covers wholly the small-diameter portion on the distal end side of the flexible portion. The coil wire diameter is preferably 0;01 to 0.3 mm, particularly 0.03 to 0.1 mm.

With the distal end portion of the wire portion 25 covered by the coil portion 26, the area of contact of the distal end portion 2 with the exterior is reduced, so that sliding resistance can be reduced. As a result, operationality of the guide wire 20 is enhanced.

The outer surface of the guide wire may be coated with a resin. Particularly, the outer surface of the guide wire portion exclusive of the coil portion is preferably coated with a resin. As the resin, the above-mentioned ones can be used.

While the second material forming the surface layer is higher in rigidity than the first material forming the center layer in all of the above-described guide wires, this configuration is not limitative. On the contrary, the second material forming the surface layer may be lower in rigidity than the first material forming the center layer.

Next, a method of manufacturing a guide wire according to one embodiment of the present invention will be described.

Figure 9:
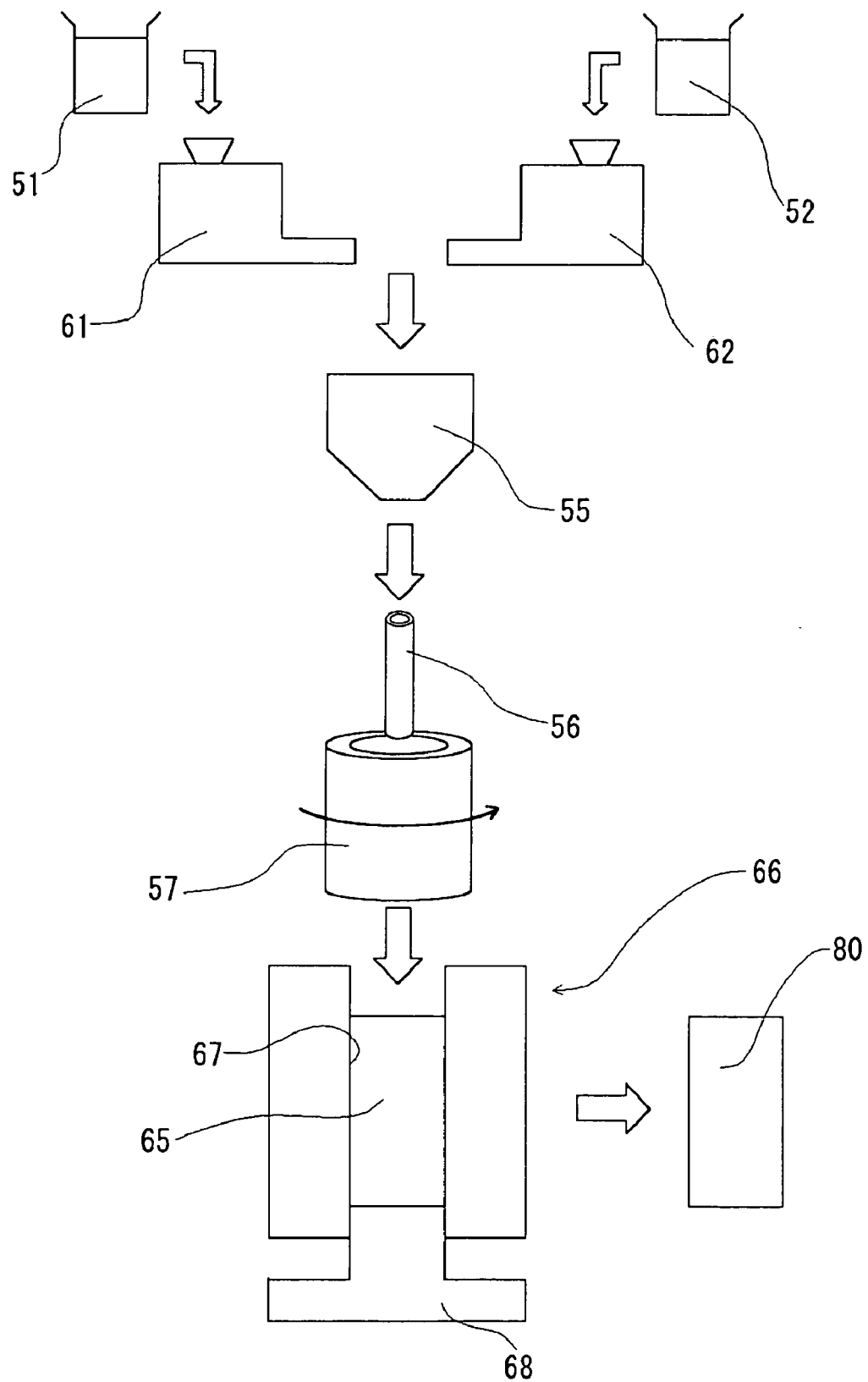
FIG. 9 is an illustration of a method of manufacturing a guide wire according to the present invention.

FIG. 9 is an illustration of the method of manufacturing a guide wire according to the one embodiment of the present invention.

This method of manufacturing a guide wire is a method of manufacturing a guide wire including a distal end portion and a main body portion, wherein the main body portion includes a center layer formed of a first material, a surface layer formed of a second material, and an intermediate layer formed of a mixture of the first material and the second material.

First, a powder of the first material and a powder of the second material are prepared. As the first material powder, preferred is a powder of any of the above-mentioned Ni—Ti based alloys; as the second material powder, preferred is a powder of any of the above-mentioned stainless steels. Particularly, an Ni—Ti alloy powder is preferable as the first material powder, and a SUS304 powder is preferable as the second material powder. As the SUS304 powder, for example, there is a stainless steel 304L powder (FEA01PB) produced by Kojundo Chemical Laboratory Co., Ltd. As the Ni—Ti alloy powder, there is a nickel-titanium alloy powder (NIA11PB) produced by Kojundo Chemical Laboratory Co., Ltd.

Then, the first material powder 51 is fed into a first material powder supply device 61, whereas the second material powder 52 is fed into a second material powder supply device 62. As the powder supply device, for example, a loss-in-weight type feeder KCL24KQX2 produced by K-Tron International, Inc. or the like is preferably used. The powder supply devices 61 and 62 each has the function of regulating continuously and variably the quantity of the powder supplied. The supply devices are so set that, for example, the quantity of the powder supplied from the second material powder supply device 62 is gradually increased from 0 to 100 g/min, for example, with the lapse of time, while the quantity of the nickel-titanium alloy powder supplied from the first material powder supply device 61 is gradually decreased from 100 to 0 g/min, for example, with the lapse of time.

Thereafter, the material powders supplied respectively from the power supply devices 61 and 62 are fed into and stirred in a powder stirrer-mixer 55. The powder flowing out of the stirrer-mixer 55 is supplied through a nozzle 56 into a hollow cylindrical body 57 which is rotated about its major axis and which is provided with top and bottom lids. Namely, the material powders are supplied from powder metering supply devices 61 and 62 and mixed by the powder stirrer-mixer 55 so that the composition of the powder continuously supplied through the nozzle 56 into the hollow cylindrical body 57 is varied. This makes it possible to obtain a powder stack having a gradient composition in the radial direction. The power stack has a structure in which the center portion is composed of the Ni—Ti alloy powder, the proportion of the stainless steel powder increases toward the peripheral portion, and the surface portion is composed of the stainless steel powder.

Then, the powder stack 65 produced as above is sintered. The sintering of the powder stack is preferably carried out by a pressure sintering method such as an HIP hot-press sintering method, a discharge plasma sintering method, and a resistance heating sintering method. Particularly, in order to obtain firm binding between the powder grains further efficiently, it is preferable to use both the hot-press method and the discharge plasma sintering method or to use the discharge plasma sintering method.

The sintering apparatus shown in the figure is a discharge plasma sintering apparatus 66, which includes a sintering chamber 67, and pressing mechanisms 68 (one of these is not shown) for pressing the stack of the mixture from both ends of the sintering chamber 67. Incidentally, the sintering apparatus may be a hot-press apparatus. The diameter of the stack (in other words, the inside diameter of the sintering chamber) is preferably 5 to 100 mm, particularly 10 to 40 mm, and the height of the stack is preferably 2 to 100 mm, particularly 5 to 20 mm. As the sintering apparatus 66, for example, a discharge plasma sintering apparatus SPS-511S produced by Sumitomo Coal Mining Co., Ltd. can be used. The pressure applied to the sintering chamber is preferably about 30 to 50 MPa. The sintering temperature is preferably about 1000 to 1600 degrees. The sintering time is preferably 10 to 30 min.

A sintered body 80 thus obtained is then reduced in diameter. The diameter-reducing process may be carried out by a method in which the diameter of the sintered body 80 is reduced to a predetermined diameter by hot roll forging, press working or the like, and, further, the diameter is further reduced by use of a wire drawing apparatus or the like until the wire diameter is reduced to the desired diameter of the main body portion of the guide wire.

Then, of the wire material produced as above, the portion for constituting the main body portion 3 of the guide wire is left as it is, whereas the portions for constituting the intermediate portion 4 and the distal end portion 2 of the guide wire are further reduced in diameter. The diameter-reducing process for forming the distal end portion and the intermediate portion of the guide wire is carried out by mechanical grinding, chemical polishing or the like. Particularly, the intermediate portion is preferably so processed that the layer containing the second material forming the surface layer in a high content is gradually decreased in thickness, as in the embodiment shown in FIG. 1. Furthermore, the distal end portion is so produced that a layer containing the second material is a little formed or is not formed at all.

Incidentally, while an example in which the center layer of the guide wire is composed of the Ni—Ti alloy whereas the surface layer is composed of the stainless steel has been described in the above embodiment, the compositions may be contrary to the above.

Figure 10:
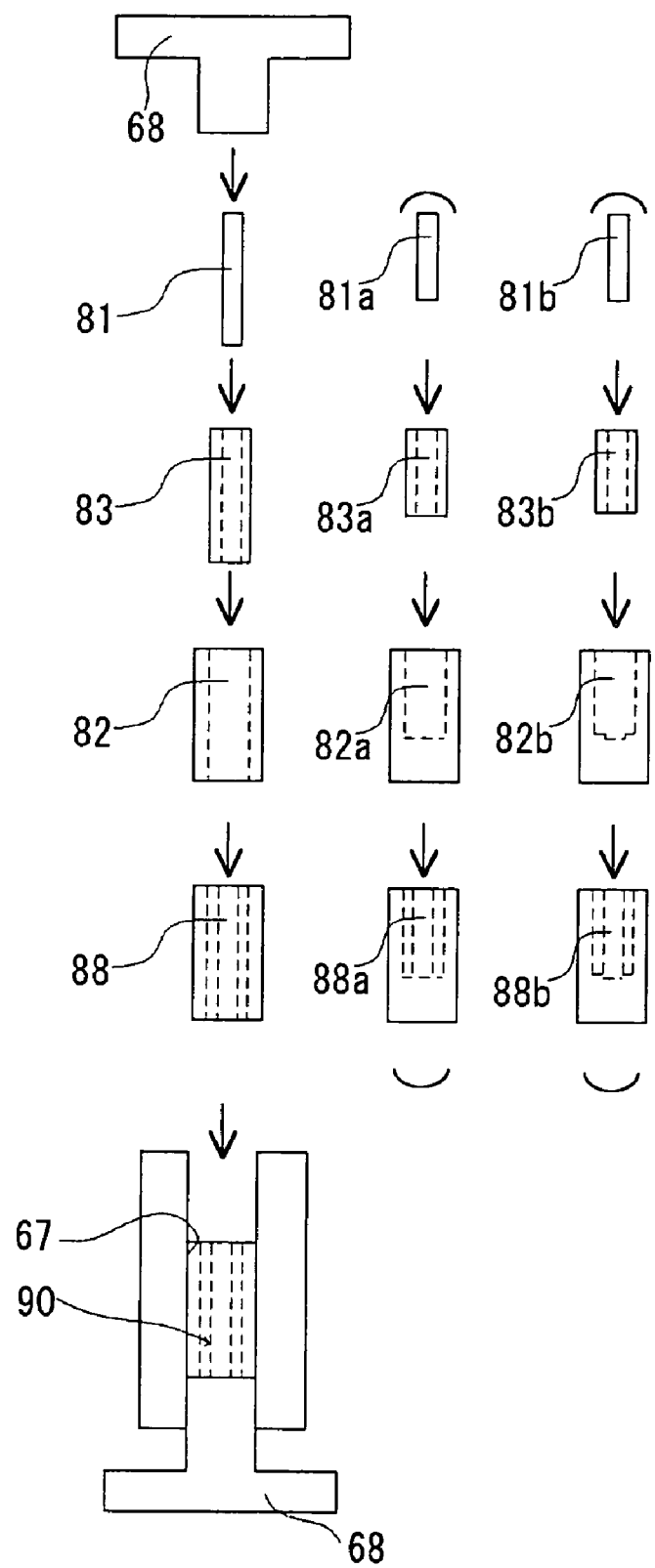
FIG. 10 is an illustration of another method of manufacturing a guide wire according to the present invention.

In addition, the method of manufacturing a guide wire according to the present invention may be as described below. FIG. 10 is an illustration of a method of manufacturing a guide wire according to another embodiment of the present invention.

The method of manufacturing a guide wire in this embodiment differs from the above-described method of manufacturing a guide wire only in the step of forming a sintered body 80. The other points of the manufacturing method in this embodiment are the same as those in the above-described method of manufacturing a guide wire. Now, only the different point will be described below.

As has been described above, the first material powder and the second material powder are prepared. As the first metallic material, any of those materials described above is used. Among the usable materials, preferred are Ni—Ti based alloys, and more preferred are Ni—Ti alloys. As the second metallic material, any of those materials described above is used. Among the usable materials, preferred are stainless steels, and more preferred is SUS304L. Besides, the average grain diameter of the powders is preferably about 10 to 30 μm. Then, the first material powder is kneaded with a binder, to produce a first metallic powder containing material. Similarly, the second material powder is kneaded with a binder, to produce a second metallic powder containing material. Furthermore, the first material powder and the second material powder are kneaded with a binder, to produce a mixture powder containing material. The weight ratio of the first material to the second material in the mixture powder containing material is preferably in the range of from 3:7 to 7:3, more particularly from 4:6 to 6:4. As the binder, a variety of binders can be used. As the binder, for example, paraffin wax is preferable. Further, molding assistants may be added to the powder containing materials. As the molding assistant, there may be used oily agents, polyethylene, etc. The first and second metallic powder containing materials may be palletized.

Then, a cylindrical body 81 is produced by use of the first metallic powder containing material. The diameter of the cylindrical body 81 is preferably 5 to 100 mm, particularly 10 to 40 mm, and the height (length) of the cylindrical body 81 is preferably 2 to 100 mm, particularly 5 to 20 mm.

Then, a first hollow cylindrical body 83 is produced by use of the mixture powder containing material which contains the first material powder and the second material powder. The hollow cylindrical body 83 is formed to have an inside diameter substantially equal to the diameter of the cylindrical body 81. The outside diameter of the hollow cylindrical body 83 is preferably 10 to 150 mm, particularly 15 to 50 mm, and the height (length) of the hollow cylindrical body 83 is substantially equal to that of the cylindrical body 81.

Then, a second hollow cylindrical body 82 is produced by use of the second metallic powder containing material. The second hollow cylindrical body 82 is formed to have an inside diameter substantially equal to the outside diameter of the first hollow cylindrical body 83. The outside diameter of the second hollow cylindrical body 82 is preferably 15 to 200 mm, particularly 20 to 80 mm, and the height (length) thereof is substantially equal to that of the first hollow cylindrical body 83.

Subsequently, the first hollow cylindrical body 83 is contained in the second hollow cylindrical body 82, and the cylindrical body 81 is contained in the first hollow cylindrical body 83, to produce a laminate 88 for manufacturing a guide wire.

Then, a binder removing step for removing the binder or binders from the laminate 88. Specifically, the laminate 88 is inserted into a binder removing furnace (not shown), and the binder or binders are removed. The binder removing step is preferably carried out by heating. The binder removing step is preferably carried out by passing the laminate 88 through the binder removing furnace. Specifically, the binder removing step is so carried out that a certain difference exists between the temperature at the time of entrance of the laminate 88 into the binder removing furnace and a maximum heating temperature in the binder removing furnace. Namely, the temperature is lower at an inlet of the binder removing furnace, and the temperature is raised as the laminate 88 proceeds through the furnace. Incidentally, the binder removing furnace may be so set that the temperature is constant in the range from an intermediate portion to the exit side of the furnace. The temperature difference inside the binder removing furnace is preferably about 100 to 600 degrees. With the initial temperature thus set to be lower, abrupt loss of the binder(s) can be prevented. Besides, the binder removing time (the period of time from the entrance of the laminate 88 into the binder removing furnace to the discharge of the laminate 88 from the furnace) is preferably 10 to 20 min, particularly 5 to 10 min.

Next, a step of sintering the laminate 88 for manufacturing a guide wire is conducted. The sintering of the laminate 88 is preferably carried out by a pressure sintering method such as a hot-press sintering method, a discharge plasma sintering method, and a resistance heating sintering method. Particularly, in order to obtain firm binding of the powder grains further efficiently, it is preferable to use both the hot-press method and the discharge plasma sintering method or to use the discharge plasma sintering method.

The sintering apparatus shown in the figure is a discharge plasma sintering apparatus 66, which includes a sintering chamber 67, and a pressing mechanism 68 for pressing the laminate of the mixture from both ends of the sintering chamber 67. Incidentally, the sintering apparatus may be a hot-press apparatus. The diameter of the laminate (in other words, the inside diameter of the sintering chamber) is preferably 5 to 100 mm, particularly 10 to 40 mm, and the height of the laminate is preferably 2 to 100 mm, particularly 5 to 20 mm. As the sintering apparatus, for example, a discharge plasma sintering apparatus SPS-511 produced by Sumitomo Coal Mining Co., Ltd. can be used. The pressure applied to the sintering chamber is preferably about 30 to 50 MPa. The sintering temperature is preferably about 1000 to 1600 degrees. The sintering time is preferably about 10 to 30 mm.

A sintered body 90 obtained as above is then reduced in diameter. The reduction in diameter may be carried out by a method in which the sintered body 90 is reduced in diameter to a predetermined outer diameter by hot roll forging, press working or the like, and is further reduced in diameter by a wire drawing apparatus or the like until the wire diameter is reduced to the desired diameter of the main body portion of the guide wire.

Then, of the wire material produced as above, the portion for constituting the main body portion 3 of the guide wire is left as it is, whereas the portions for constituting the intermediate portion 4 and the distal end portion 21 are further reduced in diameter. This reduction in diameter for forming the distal end portion and the intermediate portion is carried out by mechanical polishing, chemical polishing or the like. Particularly, the intermediate portion is preferably so processed that a layer containing the second material forming the surface layer in a high content is gradually reduced in thickness, as in the embodiment shown in FIG. 1. Further, the distal end portion is so produced that a layer containing the second material is a little formed or is not formed at all.

Incidentally, the laminate for manufacturing the guide wire may be as shown as a laminate 88*a* in FIG. 10. In this laminate 88*a*, a second tubular body 82*a* is closed at its bottom surface and includes a column shaped recess in the inside thereof. A cylindrical body 81*a* and the first tubular body 83*a* each have a height (in other words, a length) equal to the depth of the recess in the second tubular body 82*a*. Therefore, of the laminate 88*a*, the portion ranging from a top portion to a bottom surface portion has the three-layer structure, and the bottom surface portion has a single-layer structure. With the laminate 88*a* structured as above, a proximal end portion of the main body portion of the guide wire manufactured can be formed of the second material.

Furthermore, the laminate for manufacturing a guide wire may be as shown as a laminate 88*b* in FIG. 10. In this laminate 88*b*, a second tubular body 82*b* is closed at its bottom surface and includes a column shaped recess in the inside thereof, with the column shaped recess having a dent at its center. A first tubular body 83*b* has a height (in other words, a length) equal to the depth of the recess in the second tubular body 82*b*. In addition, a columnar body 81*b* has a height (in other words, a length) equal to the depth to the dent portion in the second tubular body 82*b*. Therefore, of the laminate 88*b*, a bottom surface portion has a single-layer structure, and an upper portion has a three-layer structure, with a short two-layer structure portion provided therebetween. With the laminate 88*b* structured as above, a proximal end portion of the main body portion of the guide wire manufactured can be formed of the second material, and a transition region can be formed at a distal end portion of the proximal end portion.

According to the present invention, the guide wire has combined physical properties of the first material and the second material, and therefore has intermediate physical properties, as compared with guide wires formed only of the first material or formed only of the second material. Therefore, it is possible to obtain a guide wire which shows high operationality.

In addition, where the distal end portion is formed of the first material and is continuous with a central portion of the main body portion, a central portion of the guide wire is integral, so that the guide wire does not have a point or points of abrupt change in physical properties but shows good operationality.

Further, where the guide wire includes the intermediate portion located between the distal end portion and the main body portion and the intermediate portion includes the center layer formed of the first material and the surface layer formed of a mixture of the first material and the second material, the guide wire does not show an abrupt change in physical properties between the distal end portion and the main body portion. Therefore, the guide wire does not have a point or points of abrupt change in physical properties but shows good operationality.

Furthermore, where the intermediate layer formed of a mixture of the first material and the second material is decreased in the content of the first material and increased in the content of the second material as the surface layer is approached, the guide wire has gradient physical properties in the radial direction, resulting in that inter-layer exfoliation and the like are prevented from occurring.

In addition, where the first material is a first metallic material and the second material is a second metallic material higher in rigidity than the first metallic material, the guide wire obtained shows a further enhanced operationality.

Where the guide wire includes the coil portion so provided as to cover the distal end portion of the guide wire, the operation of inserting the guide wire into a target cite in a living body is easier to perform.

Where the guide wire is an integral body free of any joint portion, the guide wire does not have a point or point of abrupt change in physical properties but shows good operationality.

The invention claimed is:

1. A guide wire comprising a distal end portion and a main body portion, wherein said main body portion includes a center layer comprising a first material, a surface layer comprising a second material and defining an outermost periphery of said main body portion, and an intermediate layer having a predetermined thickness and a predetermined length comprising a mixture of said first material and said second material, wherein the mixture of said first material and said second material in said intermediate layer has a decreased proportion of said first material toward said surface layer and an increased proportion of said second material toward said surface layer,
    wherein a weight ratio of the first material to the second material in the material for forming the intermediate layer is in the range of 1:9 to 9:1,
    wherein said main body portion has a structure in which said center layer, said intermediate layer, and said surface layer are provided in this order from a center of said main body portion toward the outermost periphery of said main body portion,
    wherein said first material is a Ni-Ti based alloy, and
    wherein said second material is a metallic material higher in rigidity than said Ni-Ti based alloy.

2. A guide wire according to claim 1, wherein said distal end portion is formed of said first material, and is continuous with said center layer of said main body portion.

3. A guide wire according to claim 1, comprising an intermediate portion located between said distal end portion and said main body portion, wherein said intermediate portion comprises said center layer formed of said first material, and said surface layer formed of a mixture of said first material and said second material.

4. A guide wire according to claim 1, wherein said second material is a stainless steel.

5. A guide wire according to claim 1, wherein a weight ratio of the first material to the second material in the material for forming the intermediate layer is in the range of 3:7 to 7:3.

6. A guide wire according to claim 1, wherein said main body portion is formed by a sintered body, said sintered body having said center layer, said surface layer, and said intermediate layer, wherein said center layer is formed by sintering said first material, said surface layer is formed by sintering said second material, and said intermediate layer is formed by sintering said mixture of said first material and said second material.

7. A guide wire according to claim 1, wherein said main body portion is formed by a sintered body, said sintered body including said center layer, said surface layer, and said intermediate layer, wherein said center layer includes a sintered body of said first material, said surface layer includes a sintered body of said second material, and said intermediate layer includes a sintered body of said mixture of said first material and said second material.

8. A guide wire comprising a distal end portion, a main body portion, and an intermediate portion located between said distal end portion and said main body portion,
    wherein said intermediate portion includes a center layer comprising a first material, and a surface layer comprising a mixture of said first material and a second material, said surface layer covering said center layer and defining an outermost periphery of said intermediate portion,
    and wherein said surface layer is decreased in a content of said first material toward the outermost periphery of said intermediate portion and increased in a content of said second material toward the outermost periphery of said intermediate portion such that said surface layer has gradient physical properties in a radial direction.

9. A guide wire according to claim 8, wherein said second material is a material higher in rigidity than said first material.

10. A guide wire according to claim 8, wherein a content of the second material in said surface layer is increased stepwise or increased gradually toward the outermost periphery of said intermediate portion.

11. A guide wire comprising a distal end portion and a main body portion, wherein said main body portion includes a center layer comprising a first material, a surface layer comprising a second material, and an intermediate layer comprising a mixture of said first material and said second material, wherein said main body portion has a structure in which said center layer, said intermediate layer, and said surface layer are provided in this order from a center of said main body portion toward an outermost periphery of said main body portion,
    wherein said intermediate layer is increased stepwise or gradually in a content of said first material toward said center layer, and
    wherein said first material is a first metallic material, said second material is a second metallic material higher in rigidity than said first metallic material, and said second metallic material is stainless steel.

* * * * *